(12) United States Patent
Farazi et al.

(10) Patent No.: US 8,521,277 B2
(45) Date of Patent: Aug. 27, 2013

(54) IMPLANTABLE SYSTEMS AND METHOD FOR USE THEREWITH FOR TRACKING CHANGES IN HEMODYNAMICS AND CARDIAC DISEASE

(75) Inventors: Taraneh Ghaffari Farazi, San Jose, CA (US); Fujian Qu, Sunnyvale, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1144 days.

(21) Appl. No.: 12/204,683

(22) Filed: Sep. 4, 2008

(65) Prior Publication Data

US 2010/0057155 A1 Mar. 4, 2010

(51) Int. Cl.
*A61N 1/362* (2006.01)

(52) U.S. Cl.
USPC .......... 607/6; 607/9; 607/14; 607/23; 607/27; 607/28; 600/486; 600/518

(58) Field of Classification Search
None
See application file for complete search history.

(56) References Cited

U.S. PATENT DOCUMENTS

| | | | |
|---|---|---|---|
| 5,184,615 A * | 2/1993 | Nappholz et al. | 607/14 |
| 5,458,623 A * | 10/1995 | Lu et al. | 607/28 |
| 5,840,038 A | 11/1998 | Xue et al. | |
| 6,129,744 A | 10/2000 | Boute | |
| 6,516,225 B1 | 2/2003 | Florio | |
| 6,618,622 B1 | 9/2003 | Mann et al. | |
| 6,711,439 B1 | 3/2004 | Bradley et al. | |
| 6,937,887 B2 | 8/2005 | Bock | |
| 7,010,346 B1 | 3/2006 | Schloss et al. | |
| 7,062,327 B2 | 6/2006 | Bradley et al. | |
| 7,072,715 B1 | 7/2006 | Bradley | |
| 7,349,738 B1 | 3/2008 | Bradley et al. | |
| 7,440,804 B1 * | 10/2008 | Min et al. | 607/28 |
| 2006/0276848 A1 | 12/2006 | Min et al. | |

FOREIGN PATENT DOCUMENTS

| | | |
|---|---|---|
| EP | 1731088 A1 | 12/2006 |
| WO | 2007038861 A1 | 4/2007 |

OTHER PUBLICATIONS

Camsari et al., "Long-term effects of beta blocker therapy on P-wave duration and dispersion in congestive heart failure patients: a new effect?" J Electrocardiol., Apr. 2003, vol. 36(2):111-116.

DiDomenico et al., "Current issues influencing treatment strategies for acute decompensated heart failure," 40th American Society of Health System Pharmacists Midyear Clinical Meeting, Las Vegas, Nevada, Dec. 5-6, 2005.

Dixen et al., "Prolonged signal-averaged P wave duration as a prognostic marker for morbidity and mortality in patients with congestive heart failure," Scand Cardiovasc J., Sep. 2003, vol. 37. (4): 193-8.

Faggiano et al., "Contribution of Left Atrial Pressure and Dimension to Signal-Averaged P-wave Duration in Patients with Chronic Congestive Heart Failure," The American Journal of Cardiology, vol. 79(2), Jan. 15, 1997, pp. 219-222.

(Continued)

Primary Examiner — Kennedy Schaetzle
(74) Attorney, Agent, or Firm — Steven M. Mitchell

(57) ABSTRACT

Embodiments of the present invention relate to monitoring a patient's atrial stretch, heart failure (HF) condition, and/or risk of atrial fibrillation (AF), as well as methods for estimating a change in at least one of a patient's left atrial pressure (LAP), pulmonary capillary wedge pressure (PCWP), and right pulmonary artery pressure (RPAP). Embodiments of the present invention also relate to selecting a pacing energy level. Such embodiments involve determining atrial evoked response metrics when a patient's atrium is paced, and monitoring changes in such metrics.

22 Claims, 6 Drawing Sheets

(56) References Cited

OTHER PUBLICATIONS

Mantymaa et al., "Atrial Stretch Induces Rapid Increase in Brain Natriuretic Peptide but not in Atrial Natriuretic Peptide Gene Expression in Vitro," Endocrinology, vol. 133(3), pp. 1470-1473, 1993.

Song et al., "Effect of diuresis on P-Wave Duration and Dispersion," Pharmacotherapy, 2002, vol. 22:564-568.

Yamada et al., "Prediction of paroxysmal atrial fibrillation in patients with congestive heart failure: a prospective study," J Am Coll Cardiol, 2000; 35:405-413.

* cited by examiner

IMPLANTABLE SYSTEMS AND METHOD FOR USE THEREWITH FOR TRACKING CHANGES IN HEMODYNAMICS AND CARDIAC DISEASE

FIELD OF THE INVENTION

Embodiments of the present invention relate to implantable cardiac systems, and methods for use therewith.

BACKGROUND

Neutral endopeptidase (NEP) is an enzyme responsible for the metabolism of atrial natriuretic peptide (ANP). Inhibition of NEP results in increased ANP concentrations, which in turn leads to natriuresis, diuresis and decreases in intravascular volume, venous return and blood pressure. ANP is released by atrial myocytes in response to atrial stretch. Elevated plasma concentrations of ANP have been demonstrated as a potential compensatory mechanism in various disease states, including congestive heart failure, renal failure, essential hypertension and cirrhosis. Accordingly, chronic monitoring of atrial stretch may be useful, e.g., for indirect monitoring of ANP concentration.

Heart failure (HF) is a condition in which a patient's heart works less efficiently than it should, resulting in the heart failing to supply the body sufficiently with the oxygen rich blood it requires, either at exercise or at rest. Congestive heart failure (CHF) is heart failure accompanied by a build-up of fluid pressure in the pulmonary blood vessels that perfuse the lungs. Transudation of fluid from the pulmonary veins into the pulmonary interstitial spaces, and eventually into the alveolar air spaces, is called pulmonary edema, and can cause shortness of breath, hypoxia, acidosis, respiratory arrest, and even death.

Chronic diseases such as CHF require close medical management to reduce morbidity and mortality. Because the disease status evolves with time, frequent physician follow-up examinations are typically necessary. At follow-up, the physician may make adjustments to the drug regimen in order to optimize therapy. This conventional approach of periodic follow-up is unsatisfactory for some diseases, such as CHF, in which acute, life-threatening exacerbations can develop between physician follow-up examinations.

Atrial Fibrillation (AF) is a very common supraventricular tachycardia (SVT) which leads to approximately one fifth of all strokes, and is the leading risk factor for ischemic stroke. However, AF is often asymptomatic and intermittent, which typically results in appropriate diagnosis and/or treatment not occurring in a timely manner.

It is believed that chronic monitoring of the pressures within the chambers of the heart will be important in future cardiac pulse generator applications. To monitor CHF status, clinicians ideally would like to know left ventricular end-diastolic pressure (LVEDP). However, it is rarely possible to directly measure LVEDP because of the invasiveness required of a transducer capable of making such a measurement. An alternative is to measure left atrial pressure (LAP) at a time when the pressure in the left atrium and left ventricle is the same, namely at the end of an atrial contraction, when the mitral valve (located between the left and right atrium) is still open.

There is also a desired to measure pulmonary capillary wedge pressure (PCWP). PCWP is typically measured by inserting balloon-tipped, multi-lumen catheter (Swan-Ganz catheter) into a peripheral vein, then advancing the catheter into the right atrium, right ventricle, pulmonary artery, and then into a branch of the pulmonary artery. Just behind the tip of the catheter is a small balloon that can be inflated with air (~1 cc). The catheter has one opening (port) at the tip (distal to the balloon) and a second port several centimeters proximal to the balloon. These ports are connected to pressure transducers. When properly positioned in a branch of the pulmonary artery, the distal port measures pulmonary artery pressure (~25/10 mmHg) and the proximal port measures right atrial pressure (~0-3 mmHg). The balloon is then inflated, which occludes the branch of the pulmonary artery. When this occurs, the pressure in the distal port rapidly falls, and after several seconds, reaches a stable lower value that is very similar to left atrial pressure (normally about 8-10 mmHg). The balloon is then deflated. The same catheter can be used to measure cardiac output by the thermodilution technique. The pressure recorded during balloon inflation is similar to left atrial pressure because the occluded vessel, along with its distal branches that eventually form the pulmonary veins, acts as a long catheter that measures the blood pressures within the pulmonary veins and left atrium.

Measures of PCWP and/or LAP can be used to diagnose the severity of left ventricular failure and to quantify the degree of mitral valve stenosis. Both of these conditions elevate LAP and therefore PCWP. Aortic valve stenosis and regurgitation, and mitral regurgitation also elevate LAP and PCWP. When these pressures are sufficiently high, pulmonary edema may be present, which is a life-threatening condition. Note that LAP is the outflow or venous pressure for the pulmonary circulation and increases in LAP are transmitted almost fully back to the pulmonary capillaries thereby increasing their filtration.

Measures of PCWP can also be used to monitor pulmonary hypertension. Pulmonary hypertension is often caused by an increase in pulmonary vascular resistance. To calculate this, pulmonary blood flow (usually measured by the thermodilution technique), pulmonary artery pressure and PCWP measurements are typically required. Pulmonary hypertension can also result from increases in pulmonary venous pressure and pulmonary blood volume secondary to left ventricular failure or mitral or aortic valve disease.

PCWP is also useful in evaluating blood volume status when fluids are administered during hypotensive shock. One practice is to administer fluids at a rate that maintains PCWP within a desired range.

P-wave-duration (PWD) and P-wave-dispersion (Pd) in body surface electrocardiograms (ECGs) have been used by electro-physiologists (EPs) as noninvasive markers of intra-atrial conduction disturbances that predispose patients to AF. For example, an article by Yamada et al., entitled "Prediction of paroxysmal atrial fibrillation in patients with congestive heart failure: a prospective study," (J Am Coll Cardiol 2000; 35:405-13), demonstrated that attacks of paroxysmal AF occurred more frequently in patients (32%) with an abnormal P-wave signal-average electrogram (P-SAECG) than in those without (2%) an abnormal P-SAECG. The Yamada et al. article also concluded that patient's with CHF who developed proxysmal AF had a significantly longer duration of signal-averaged P-wave in body surface ECGs than those without.

An article by Faggiano et al., entitled "Contribution of left atrial pressure and dimension to signal averaged P-wave duration in patients with chronic congestive heart failure" (Am J Cardiol 1997; 179:219-22), observed that in patient's with CHF, signal averaged P-wave duration in body surface ECGs increase with an increase in pulmonary capillary wedge pressure (PCWP).

Further, an article by Song et al., entitled "Effect of diuresis on P-wave duration and dispersion" (Pharmaco therapy 2002;

22:564-8), observed that signal averaged P-wave duration in body surface ECGs increase with an increase the presence of fluid overload during heart failure decompensation, and decrease with administration of diuretics.

There is also a desire to monitor right pulmonary artery pressure (RPAP), e.g., for the purpose of indirectly monitoring the hemodynamic response to fluid therapy, medication and other treatments. RPAP is typically measured using a balloon-tipped multi-lumen catheter, similar to the one described above.

SUMMARY

Certain embodiments of the present invention relate to methods for monitoring arterial stretch, and implantable cardiac systems capable of performing such methods. For each of a plurality of periods of time during which the atrium is paced to provoke an atrial evoked response, an atrial intracardiac electrogram (IEGM) is obtained (using a chronically implanted cardiac device and at least one chronically implanted lead), wherein the atrial IEGM is indicative of atrial electrical activity of a patient's heart during the period of time. Additionally, at least one atrial evoked response metric indicative of atrial electrical activity during the period of time is determined (based on the atrial IEGM) and information about the metric(s) is stored, for each of the plurality of periods of time. Based on the stored information, a change in the atrial evoked response metric(s) over time is detected, and atrial stretch is monitored based on the detected change in the atrial evoked response metric(s) over time.

In accordance with an embodiment, the plurality of periods of time during which the atrium is paced to provoke an atrial evoked response are different times that atrial automatic capture threshold detection is performed.

In accordance with an embodiment, a change in the patient's heart failure (HF) condition can be determined based on the monitored atrial stretch, and/or a risk of an acute HF exacerbation can be predicted based on the monitored atrial stretch. In another embodiment, a change in the patient's risk of atrial fibrillation (AF) is determined based on the monitored atrial stretch.

In accordance with an embodiment, a response is triggered if a change in atrial stretch exceeds a specified threshold, and/or if a change in the atrial evoked response metric(s) is in a direction indicative of an increased atrial stretch beyond a specified threshold.

The atrial evoked response metric(s) can be atrial evoked response maximum amplitude, atrial evoked response minimum amplitude, atrial evoked response peak-to-peak amplitude, atrial evoked response duration, atrial evoked response area, atrial evoked response slope and/or atrial evoked response timing. The atrial evoked response metric(s) can alternative, or additionally, be the dispersion of one or more of the above metrics. The dispersion of a metric can be determined by calculating the standard deviation, interquartile range, range, mean difference, median absolute deviation, average absolute deviation (or simply average deviation), coefficient of variation, quartile coefficient of dispersion, relative mean difference, variance (the square of the standard deviation) or variance-to-mean ratio of the metric.

Further embodiments of the present invention relate to methods for monitoring a patient's left atrial pressure (LAP), pulmonary capillary wedge pressure (PCWP) and/or right pulmonary artery pressure (RPAP), and implantable cardiac systems capable of performing such methods. For each of a plurality of periods of time during which the atrium is paced to provoke an atrial evoked response, an atrial intracardiac electrogram (IEGM) is obtained (using a chronically implanted cardiac device and at least one chronically implanted lead), wherein the atrial IEGM is indicative of atrial electrical activity of a patient's heart during the period of time. Additionally, at least one atrial evoked response metric indicative of atrial electrical activity during the period of time is determined (based on the atrial IEGM) and information about the metric(s) is stored, for each of the plurality of periods of time. Based on the stored information, a change in the atrial evoked response metric(s) over time is detected, and a change in the patient's LAP, PCWP and RPAP is monitored based on the detected change in the atrial evoked response metric(s) over time.

Further embodiments of the present invention relate to methods for monitoring a patient's risk of atrial fibrillation (AF), and implantable cardiac systems capable of performing such methods. For each of a plurality of periods of time during which the atrium is paced to provoke an atrial evoked response, an atrial intracardiac electrogram (IEGM) is obtained (using a chronically implanted cardiac device and at least one chronically implanted lead), wherein the atrial IEGM is indicative of atrial electrical activity of a patient's heart during the period of time. Additionally, at least one atrial evoked response metric indicative of atrial electrical activity during the period of time is determined (based on the atrial IEGM) and information about the metric(s) is stored, for each of the plurality of periods of time. Based on the stored information, a change in the atrial evoked response metric(s) over time is detected, and a change in the patient's risk of AF is detected based on the detected change in the atrial evoked response metric(s) over time.

Further embodiments of the present invention relate to methods for selecting a preferred atrial pacing energy level, and implanted cardiac systems capable of performing such methods. In accordance with an embodiment, an atrial capture threshold is determined for pacing in the atrium using at least one chronically implanted lead. Based on the atrial capture threshold, a first atrial pacing energy level that provides for reliable capture of the atrium is determined. For example, the first atrial pacing energy level can be the atrial capture threshold plus a specified margin (e.g., a safety margin or working margin). At least one atrial evoked response metric is determined for one or more atrial evoked response that occurs in response to atrial pacing at the first atrial pacing energy level. At least one atrial evoked response metric is also determined for one or more atrial evoked response that occurs in response to atrial pacing at one or more energy level greater than the first energy level. A preferred atrial pacing energy level is selected to use for atrial pacing based on the determined P-wave metrics. For example, this can include selecting an atrial pacing energy level greater than the first atrial pacing energy level as the preferred atrial pacing energy level, if it is determined that atrial stretch is reduced, a patient's HF condition is improved and/or the patient's risk of AF is reduced by using an atrial pacing energy level greater than the first energy level.

This summary is not intended to be a complete description of, or limit the scope of, the invention. Alternative and additional features, aspects, and objects of the invention can be obtained from a review of the specification, the figures, and the claims.

DETAILED DESCRIPTION

The following description is of the best modes presently contemplated for practicing various embodiments of the present invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Articles, such as those discussed above in the Background, have discussed how certain metrics of intrinsic P-waves, measured from body surface ECGs (e.g., obtained using acute and non-implanted Holter devices), statistically relate to certain disorders and pressure measurements. However, such article have not disclosed nor suggested how such metrics of intrinsic P-waves can be used outside of a clinical setting. Further, such article have not taught or suggested how metrics of paced P-waves (atrial evoked responses) can be used in the role of clinical management for patients. Further, such articles have not taught or suggested how certain metrics of atrial evoked response can be obtained using an implanted cardiac device, to provide for chronic patient monitoring, and to automatically trigger various responses when appropriate.

Embodiments of the present relate to methods for use by chronically implanted systems, as well as to chronically implanted systems, that determine (e.g., measure) metrics of atrial evoked response to monitor atrial stretch, track and trend HF, predict onset of acute decompensation, estimate LAP, PCWP and/or RPAP, as well as to track and predict a risk of AF. Embodiments of the present invention also relate to methods for use by chronically implanted systems, as well as to chronically implanted systems, that select an atrial pacing energy level. An exemplary implantable cardiac system will thus be described in conjunction with FIGS. 1 and 2, in which embodiments of the present invention described herein could be implemented.

Exemplary Implantable System

Figure 1:
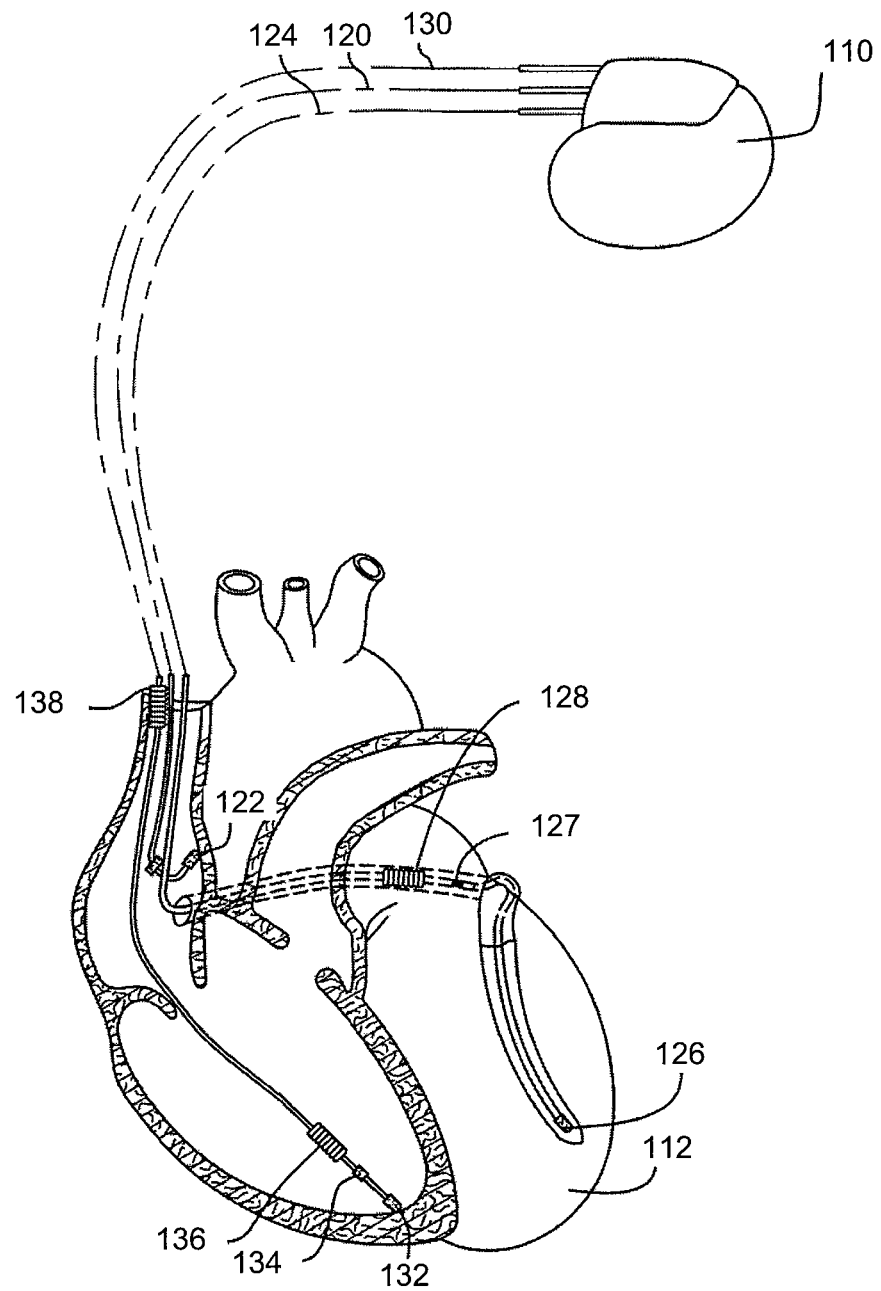
FIG. 1 is a simplified, partly cutaway view illustrating an implantable stimulation device in electrical communication with at least three leads implanted into a patient's heart for delivering multi-chamber stimulation and shock therapy and sensing cardiac activity.

Referring to FIG. 1, an exemplary chronically implantable device 110 (also referred to as a pacing device, a pacing apparatus, a stimulation device, or simply a device) is in electrical communication with a patient's heart 112 by way of three leads, 120, 124 and 130, suitable for delivering multi-chamber stimulation. The device and the leads shall often be referred to hereafter collectively as a chronically implantable system. While not necessary to perform embodiments of the present invention, the exemplary device 110 is also capable of delivering shock therapy.

To sense atrial cardiac signals and to provide right atrial chamber stimulation, the stimulation device 110 is coupled to an implantable right atrial lead 120 having at least an atrial tip electrode 122, which typically is implanted in the patient's right atrial appendage. To sense left atrial and ventricular cardiac signals and to provide left-chamber pacing therapy, the stimulation device 110 is coupled to a "coronary sinus" lead 124 designed for placement in the "coronary sinus region" via the coronary sinus for positioning a distal electrode adjacent to the left ventricle and/or additional electrode (s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 124 is designed to receive left atrial and ventricular cardiac signals and to deliver left atrial and ventricular pacing therapy using at least a left ventricular tip electrode 126, left atrial pacing therapy using at least a left atrial ring electrode 127, and shocking therapy using at least a left atrial coil electrode 128. The present invention may of course be practiced with a coronary sinus lead that does not include left atrial sensing, pacing or shocking electrodes.

The stimulation device 110 is also shown in electrical communication with the patient's heart 112 by way of an implantable right ventricular lead 130 having, in this embodiment, a right ventricular tip electrode 132, a right ventricular ring electrode 134, a right ventricular (RV) coil electrode 136, and an SVC coil electrode 138. Typically, the right ventricular lead 130 is transvenously inserted into the heart 112 so as to place the right ventricular tip electrode 132 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals and delivering stimulation in the form of pacing and shock therapy to the right ventricle. It will be understood by those skilled in the art that other lead and electrode configurations such as epicardial leads and electrodes may be used in practicing the invention. More generally, electrodes may be positioned endocardially, epicardially or pericardially.

Figure 2:
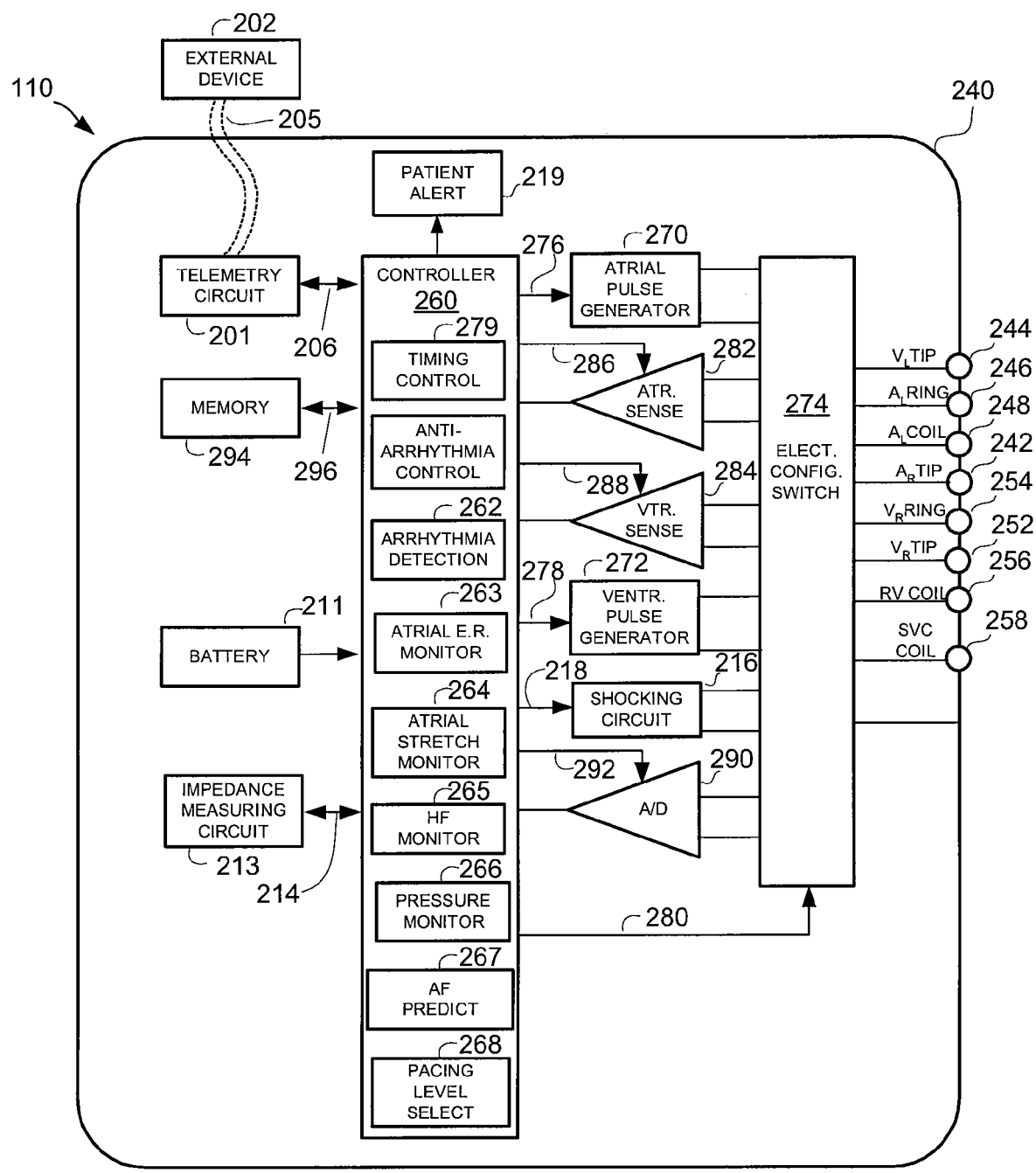
FIG. 2 is a functional block diagram of the multi-chamber implantable stimulation device of FIG. 1, illustrating the basic elements that provide pacing stimulation, cardioversion, and defibrillation in four chambers of the heart.

As illustrated in FIG. 2, a simplified block diagram is shown of the multi-chamber implantable implantable device 110, which is capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation.

The housing 240 for the implantable device 110, shown schematically in FIG. 2, is often referred to as the "can", "case" or "case electrode" and may be programmably selected to act as the return electrode for all "unipolar" modes. The housing 240 may further be used as a return electrode alone or in combination with one or more of the coil electrodes, 128, 136 and 138, for shocking purposes. The housing 240 further includes a connector (not shown) having a plurality of terminals, 242, 244, 246, 248, 252, 254, 256, and 258 (shown schematically and, for convenience, the names of the electrodes to which they are connected are shown next to the terminals). As such, to achieve right atrial sensing and pacing, the connector includes at least a right atrial tip terminal ($A_R$ TIP) 242 adapted for connection to the atrial tip electrode 122.

To achieve left atrial and ventricular sensing, pacing and shocking, the connector includes at least a left ventricular tip terminal ($V_L$ TIP) 244, a left atrial ring terminal ($A_L$ RING) 246, and a left atrial shocking terminal ($A_L$ COIL) 148, which are adapted for connection to the left ventricular ring electrode 126, the left atrial tip electrode 127, and the left atrial coil electrode 128, respectively.

To support right ventricle sensing, pacing and shocking, the connector further includes a right ventricular tip terminal ($V_R$ TIP) 252, a right ventricular ring terminal ($V_R$ RING) 254, a right ventricular shocking terminal ($R_V$ COIL) 256, and an SVC shocking terminal (SVC COIL) 258, which are adapted for connection to the right ventricular tip electrode 132, right ventricular ring electrode 134, the RV coil electrode 136, and the SVC coil electrode 138, respectively.

At the core of the implantable device 110 is a programmable microcontroller 260 which controls the various types and modes of stimulation therapy. As is well known in the art, the microcontroller 260 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design of the microcontroller 260 are not critical to the present invention. Rather, any suitable microcontroller 260 can be used to carry out the functions described herein. The use of microprocessor-based control circuits for performing timing and data analysis functions are well known in the art. In specific embodiments of the present invention, the microcontroller 260 performs some or all of the steps associated with arrhythmia detection and myocardial ischemia detection.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

An atrial pulse generator 270 and a ventricular pulse generator 272 generate pacing stimulation pulses for delivery by the right atrial lead 120, the right ventricular lead 130, and/or the coronary sinus lead 124 via an electrode configuration switch 274. It is understood that in order to provide stimulation therapy in each of the four chambers of the heart, the atrial and ventricular pulse generators, 270 and 272, may include dedicated, independent pulse generators, multiplexed pulse generators, or shared pulse generators. The pulse generators, 270 and 272, are controlled by the microcontroller 260 via appropriate control signals, 276 and 278, respectively, to trigger or inhibit the stimulation pulses.

The microcontroller 260 further includes timing control circuitry 279 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, etc.) by selectively closing the appropriate combination of switches (not shown) as is known in the art.

Atrial sensing circuits 282 and ventricular sensing circuits 284 may also be selectively coupled to the right atrial lead 120, coronary sinus lead 124, and the right ventricular lead 130, through the switch 274 for detecting the presence of cardiac activity in each of the four chambers of the heart. Accordingly, the atrial (ATR. SENSE) and ventricular (VTR. SENSE) sensing circuits, 282 and 284, may include dedicated sense amplifiers, multiplexed amplifiers, or shared amplifiers. The switch 274 determines the "sensing polarity" of the cardiac signal by selectively closing the appropriate switches, as is also known in the art. In this way, the clinician may program the sensing polarity independent of the stimulation polarity.

Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables the device 110 to deal effectively with the difficult problem of sensing the low amplitude signal characteristics of atrial or ventricular fibrillation. Such sensing circuits, 282 and 284, can be used to determine cardiac performance values used in the present invention. Alternatively, an automatic sensitivity control circuit may be used to effectively deal with signals of varying amplitude.

The outputs of the atrial and ventricular sensing circuits, 282 and 284, are connected to the microcontroller 260 which, in turn, are able to trigger or inhibit the atrial and ventricular pulse generators, 270 and 272, respectively, in a demand fashion in response to the absence or presence of cardiac activity, in the appropriate chambers of the heart. The sensing circuits, 282 and 284, in turn, receive control signals over signal lines, 286 and 288, from the microcontroller 260 for purposes of measuring cardiac performance at appropriate times, and for controlling the gain, threshold, polarization charge removal circuitry (not shown), and timing of any blocking circuitry (not shown) coupled to the inputs of the sensing circuits, 282 and 286. The sensing circuits can be used to acquire IEGM signals, which can be used to measure atrial evoked response metrics, in accordance with embodiments of the present invention.

For arrhythmia detection, the device 110 includes an arrhythmia detector 262 that utilizes the atrial and ventricular sensing circuits, 282 and 284, to sense cardiac signals to determine whether a rhythm is physiologic or pathologic. The timing intervals between sensed events (e.g., P-waves, R-waves, and depolarization signals associated with fibrillation) are then classified by the microcontroller 260 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). The arrhythmia detector 262 can be implemented within the microcontroller 260, as shown in FIG. 2. Thus, this detector 262 can be implemented by software, firmware, or combinations thereof. It is also possible that all, or portions, of the arrhythmia detector 262 can be implemented using hardware. Further, it is also possible that all, or portions, of the arrhythmia detector 262 can be implemented separate from the microcontroller 260.

In accordance with embodiments of the present invention, the implantable device 110 also includes an atrial evoked response monitor 263, that can measure atrial evoked response metrics (i.e., metrics of paced P-waves) of atrial IEGMs obtained, e.g., using the right atrial lead 120, but not limited thereto. The atrial evoked response monitor 263 can be implemented within the microcontroller 260, as shown in FIG. 2. Thus, the atrial evoked response monitor 263 can be implemented by software, firmware, or combinations thereof. It is also possible that all, or portions, of the monitor 263 can be implemented using hardware. Further, it is also possible that all, or portions, of the atrial evoked response monitor 263 can be implemented separate from the microcontroller 260. As the term is used herein, an atrial evoked response is an electrical signal arising from atrial cardiac tissue depolarization in response to delivery of an atrial pacing pulse. Stated another way, an atrial evoked response is a paced atrial event.

In accordance with embodiments of the present invention, the implantable device 110 also includes an atrial stretch monitor 264, that monitors a patient's atrial stretch using embodiments of the present invention, which are described in detail below. The atrial stretch monitor 264 can be implemented within the microcontroller 260, as shown in FIG. 2. Thus, the atrial stretch monitor 264 can be implemented by software, firmware, or combinations thereof. It is also possible that all, or portions, of the monitor 264 can be implemented using hardware. Further, it is also possible that all, or portions, of the monitor 264 can be implemented separate from the microcontroller 260. The atrial stretch monitor 264 can include, or communicate with, a component (e.g., atrial evoked response monitor) that measures atrial evoked response metrics of an atrial IEGM.

In accordance with embodiments of the present invention, the implantable device 110 also includes an heart failure (HF) monitor 265, that monitors a patient's heart failure condition using embodiments of the present invention, which are described in detail below. The HF monitor 265 can be implemented within the microcontroller 260, as shown in FIG. 2. Thus, the HF monitor 265 can be implemented by software, firmware, or combinations thereof. It is also possible that all, or portions, of the monitor 265 can be implemented using hardware. Further, it is also possible that all, or portions, of the HF monitor 265 can be implemented separate from the microcontroller 260. The HF monitor 265 can include, or communicate with, a component (e.g., atrial stretch monitor 264) that monitors atrial stretch.

The implantable device 110 is also shown as including a pressure monitor 266, an AF predictor 267 and an pacing energy level selector 268. The pressure monitor 266 can estimate changes in LAP, PCWP and/or RPAP, in accordance with embodiments of the present invention described below. The AF predictor 267 can monitor changes in a patient's risk of AF, in accordance with embodiments of the present invention described below. The pacing energy level selector 268 can select a preferred atrial pacing energy level, in accordance with embodiments of the present invention described below. The monitor 266, predictor 267 and selector 268 can be implemented by software, firmware, or combinations thereof. It is also possible that all, or portions, of monitor 266, predictor 267 and selector 268 can be implemented using hardware. Further, it is also possible that all, or portions, of the monitor 266, predictor 267 and selector 268 can be implemented separate from the microcontroller 260. The monitor 266, predictor 267 and selector 268 can communicate with the atrial evoked response monitor 263, or each such monitor 266, predictor 267 and selector 268 can monitor atrial evoked response metrics on their own.

The implantable device can also include a patient alert 219, which produces a vibratory or auditory alert, or the like, when triggered.

Still referring to FIG. 2, cardiac signals are also applied to the inputs of an analog-to-digital (A/D) data acquisition system 290. The data acquisition system 290 is configured to acquire intracardiac electrogram signals, convert the raw analog data into a digital signal, and store the digital signals for later processing and/or telemetric transmission to an external device 202. The data acquisition system 290 is coupled to the right atrial lead 120, the coronary sinus lead 124, and the right ventricular lead 130 through the switch 274 to sample cardiac signals across any pair of desired electrodes.

The data acquisition system 290 can be coupled to the microcontroller 260, or other detection circuitry, for detecting an evoked response from the heart 112 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 260 detects a depolarization signal during a window following a stimulation pulse, the presence of which indicates that capture has occurred. The microcontroller 260 enables capture detection by triggering the ventricular pulse generator 272 to generate a stimulation pulse, starting a capture detection window using the timing control circuitry 279 within the microcontroller 260, and enabling the data acquisition system 290 via control signal 292 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 260 is further coupled to the memory 294 by a suitable data/address bus 296, wherein the programmable operating parameters used by the microcontroller 260 are stored and modified, as required, in order to customize the operation of the implantable device 110 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 112 within each respective tier of therapy. The memory 294 can also be used to store information about atrial evoked response metrics and changes in the same can be detected based on the stored information using embodiments of the present invention.

The operating parameters of the implantable device 110 may be non-invasively programmed into the memory 294 through a telemetry circuit 201 in telemetric communication with an external device 202, such as a programmer, transtelephonic transceiver, or a diagnostic system analyzer. The telemetry circuit 201 can be activated by the microcontroller 260 by a control signal 206. The telemetry circuit 201 advantageously allows intracardiac electrograms and status information relating to the operation of the device 110 (as contained in the microcontroller 260 or memory 294) to be sent to the external device 202 through an established communication link 204. The telemetry circuit 201 can also be used to trigger alarms or alerts of the external device 202, or to instruct the external device 202 to notify a caregiver regarding detection of various episodes, occurrences and changes in conditions that are detected using embodiments of the present invention.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 110 additionally includes a battery 211 which provides operating power to all of the circuits shown in FIG. 2. If the implantable device 110 also employs shocking therapy, the battery 211 should be capable of operating at low current drains for long periods of time, and then be capable of providing high-current pulses (for capacitor charging) when the patient requires a shock pulse. The battery 211 should also have a predictable discharge characteristic so that elective replacement time can be detected.

The implantable device 110 can also include a magnet detection circuitry (not shown), coupled to the microcontroller 260. It is the purpose of the magnet detection circuitry to detect when a magnet is placed over the implantable device 110, which magnet may be used by a clinician to perform various test functions of the implantable device 110 and/or to signal the microcontroller 260 that the external programmer 202 is in place to receive or transmit data to the microcontroller 260 through the telemetry circuits 201.

As further shown in FIG. 2, the device 110 is also shown as having an impedance measuring circuit 213 which is enabled by the microcontroller 260 via a control signal 214. The known uses for an impedance measuring circuit 213 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds and heart failure condition; detecting when the device has been implanted; measuring stroke volume; and detecting the opening of heart valves, etc. The impedance measuring circuit 213 is advantageously coupled to the switch 274 so that any desired electrode may be used. The impedance measuring circuit 213 is not critical to the present invention and is shown only for completeness.

In the case where the implantable device 110 is also intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 260 further controls a shocking circuit 216 by way of a control signal 218. The shocking circuit 216 generates shocking pulses of low (up to 0.5 Joules), moderate (0.5-10 Joules), or high energy (11 to 40 Joules), as controlled by the microcontroller 260. Such shocking pulses are applied to the patient's heart 112 through at least two shocking electrodes, and as shown in this embodiment, selected from the left atrial coil electrode 228, the RV coil electrode 236, and/or the SVC coil electrode 238. As noted above, the housing 240 may act as an active electrode in combination with the RV electrode 236, or as part of a split electrical vector using the SVC coil electrode 238 or the left atrial coil electrode 228 (i.e., using the RV electrode as a common electrode).

The above described implantable device 110 was described as an exemplary pacing device. One or ordinary skill in the art would understand that embodiments of the present invention can be used with alternative types of implantable devices. Accordingly, embodiments of the present invention should not be limited to use only with the above described device.

Atrial Automatic Capture Threshold Detection

The success of a cardiac pacemaker in depolarizing or "capturing" the heart relies on the pacing stimulus energy level delivered to the myocardium exceeding a threshold value, known as the capture threshold. More specifically, the capture threshold represents the amount of electrical energy required to alter the permeability of the myocardial cells to thereby initiate cell depolarization. If the energy of the pacing stimulus does not exceed the capture threshold, then the permeability of the myocardial cells will not be altered and thus no depolarization will result. In contrast, if the energy of the pacing stimulus exceeds the capture threshold, then the permeability of the myocardial cells will be altered such that depolarization will result. The energy is a function of current, voltage and pulse duration (time). Accordingly, the pacing energy level can be adjusted by adjusting one of more of current, voltage and pulse duration.

The capture threshold is not fixed, but rather, may increase and decrease during of the course of a single day, on a daily basis, as well as in response to changes in cardiac disease status. Changes in the capture threshold may be detected by monitoring the efficacy of stimulating pulses at a given energy level. If capture does not occur at a particular stimulation energy level which previously was adequate to effect capture, then it can be surmised that the capture threshold has increased and that the stimulation energy should be increased. In contrast, if capture occurs consistently at a particular stimulation energy level over a relatively large number of successive stimulation cycles, then it is possible that the capture threshold has decreased such that the stimulation energy is being delivered at level higher than necessary to effect capture. This can be checked by lowering the stimulation energy level and monitoring for capture, or loss of thereof, at the new lower energy level.

To reduce current drain on the power supply, it is desirable to automatically adjust the pacemaker such that the amount of stimulation energy delivered to the myocardium is maintained at a level that will reliably capture the heart without wasting power. Such a process has been called many things, including automatic capture threshold detection, automatic stimulation threshold search, automatic capture verification, automatic verification of capture, and Autocapture™. For the following discussion, this process will be referred to as automatic capture threshold detection.

While there are certainly variations in how and when automatic capture threshold detection can be performed, they all have a similar goal, which is generally to determine whether a delivered pacing stimulus results in stimulation of the myocardium, and, consequently, to adapt the stimulation pulses to a level somewhat above (e.g., a margin above) that which is needed to maintain capture.

Automatic capture threshold detection can be performed when a device is implanted, and from time to time thereafter so that pacing stimulation levels are appropriately adjusted as patient conditions change. For example, an automatic capture threshold detection algorithm can be performed whenever two consecutive pacing pulses fail to evoke capture, and/or may be performed periodically (e.g., every 8 hours, every 24 hours, etc). The following patents, each of which are incorporated herein by reference, provide details of various exemplary automatic capture threshold detection algorithms: U.S. Pat. No. 6,618,622 (Mann et al.) entitled "Method and Apparatus of Determining Atrial Capture Threshold While Avoiding Pacemaker Mediated Tachycardia"; U.S. Pat. No. 7,062,327 (Bradley et al.) entitled "Method and Apparatus for Providing Atrial Autocapture in a Dynamic Atrial Overdrive Pacing System for Use in an Implantable Cardiac Stimulation Device."

Depending on the pacing mode that is being used, automatic capture threshold detection can be performed in the atrium and/or in the ventricles. When performed in the atrium, this process can be referred to more specifically as atrial automatic capture threshold detection. Similarly, when performed in the ventricles, this process can be referred to more specifically as ventricular automatic capture threshold detection.

When atrial automatic capture threshold detection is being performed, the implantable cardiac device monitors for atrial conduction (i.e., atrial evoked response, also known as paced P-waves or paced atrial events) that occur in response to atrial pacing pulses. Specific embodiments of the present invention take advantage of this process by determining and storing information about the monitored atrial evoked responses, such as, but not limited to atrial evoked response duration, atrial evoked response maximum amplitude, atrial evoked response minimum amplitude, atrial evoked response peak-to-peak amplitude, atrial evoked response area, atrial evoked response slope, atrial evoked response timing, or the dispersion of any of the aforementioned metrics, and use such stored information to monitor and/or estimate changes in a cardiac condition and/or characteristic. In other words, whenever (or at least some of the times that) an atrial automatic capture threshold detection process is being performed, one or more atrial evoked response metric is measured and stored, and thereafter used for cardiac analysis above and beyond capture threshold detection. In this manner, specific embodiments of the present invention take advantage of the fact that the atrial automatic capture threshold detection process will occur from time to time by learning additional information during such process.

Atrial Stretch

Figure 3:
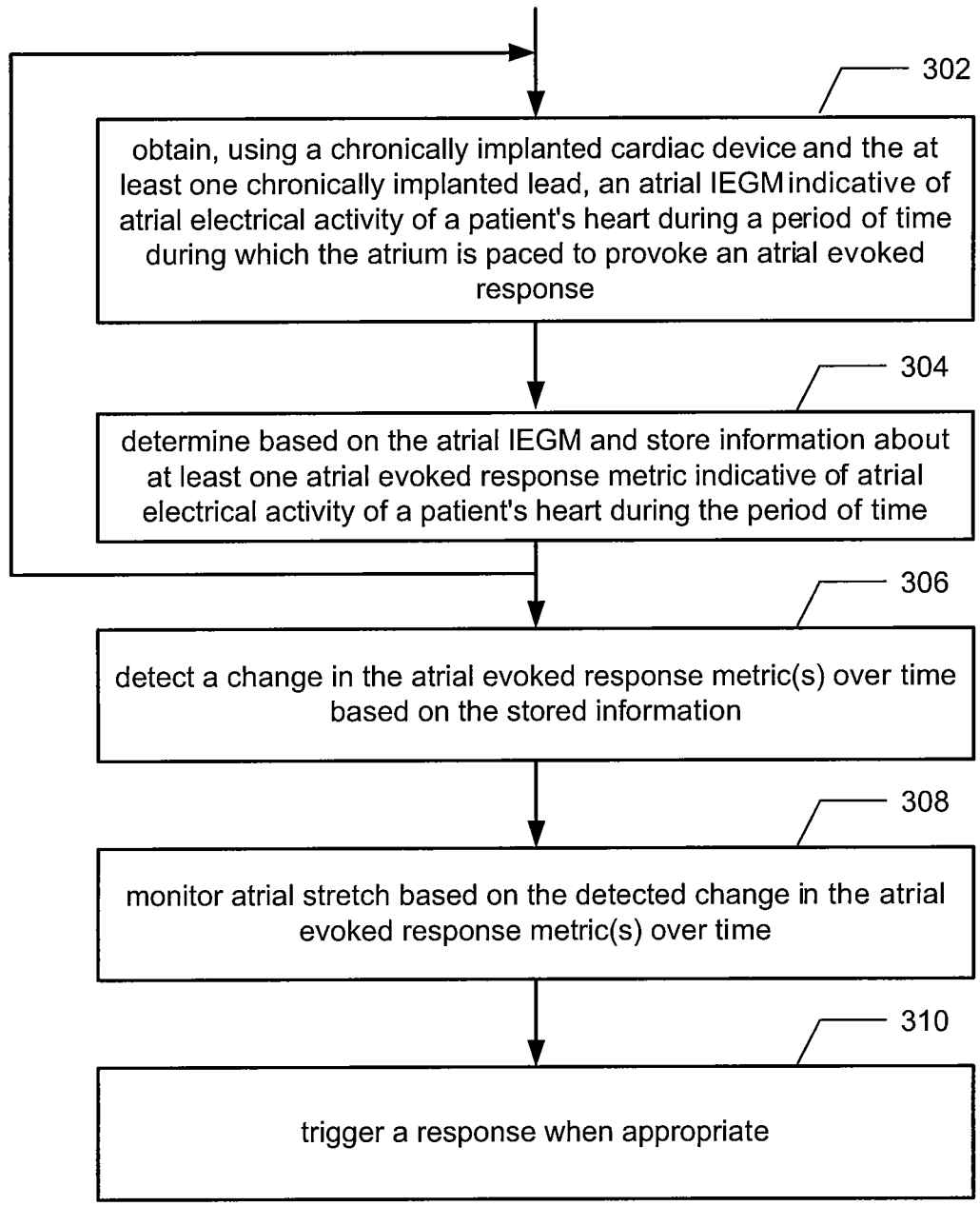
FIG. 3 is a high level flow diagram that is used to summarize specific embodiments of the present invention that can be used to monitor atrial stretch.

The high level flow diagram of FIG. 3 will now be used to describe methods for use by an implanted system including a chronically implanted cardiac device and at least one chronically implanted lead, for monitoring changes in atrial stretch. Embodiments of the present invention are also directed to chronically implanted systems that can implement such methods.

Referring to FIG. 3, at step 302, a chronically implanted cardiac device and at least one chronically implanted lead are used to obtain an atrial intracardiac electrogram (IEGM) indicative of electrical activity of a patient's heart during a period of time during which the atrium is paced to provoke an atrial evoked response. The chronically implantable cardiac device 110 and the right atrial lead 120, which were discussed above with reference to FIGS. 1 and 2, are examples of such a device and lead, but embodiments of the present invention should not be limited thereto.

At step 304, based on the atrial IEGM there is a determination of atrial evoked response metric(s) indicative of atrial electrical activity during the period of time, and information about such atrial evoked response metric(s) is stored, e.g., in memory 294 of FIG. 2. Metrics of an atrial evoked response that can be measured from an atrial IEGM, include, e.g., atrial evoked response maximum amplitude (atrial evoked response max), atrial evoked response minimum amplitude (atrial evoked response min), atrial evoked response peak-to-peak amplitude, atrial evoked response duration, atrial evoked response area, atrial evoked response slope, atrial evoked response timing, or the dispersion of one of the aforementioned metrics. For example, atrial evoked response duration dispersion can be the difference between the maximum atrial evoked response duration and the minimum atrial evoked response duration (i.e., the range of durations). The dispersion of another one of the other above mentioned metrics can alternatively or additionally be used. Also, as explained above, other measures of dispersion besides range can be used, e.g., standard deviation, interquartile range, mean difference, median absolute deviation, average absolute deviation (or simply average deviation), coefficient of variation, quartile coefficient of dispersion, relative mean difference, variance (the square of the standard deviation) or variance-to-mean ratio. Preferably, the atrial evoked response metric(s) determined at step 304, each time step 304 is repeated, is/are of the same type, so such metric(s) can be readily compared. For example, each time step 304 is performed an average atrial evoked response duration for 60 cardiac cycles and an average atrial evoked response duration dispersion for 60 cardiac cycles can be determined.

Preferably each period of time referred to in steps 302 and 304 spans a plurality of cardiac cycles, so that atrial evoked response metric(s) is/are determined for each of a plurality of cardiac cycles, and metrics of the same type (e.g., atrial evoked response duration) are combined, e.g., averaged, summed, filtered (according to signal stability and/or quality), heart rate corrected, or the like, to reduce the affects of noise and motion artifacts on such measurements. For example, the atrial evoked response durations for 60 cardiac cycles can be measured and averaged to produce an average atrial evoked response duration for a period of time lasting 60 cardiac cycles. Additionally, or alternatively, an atrial evoked response duration dispersion for the same 60 cardiac cycles can be measured an averaged to produce an average atrial evoked response dispersion for the period of time. Accordingly, in this example, the result of step 304 can be an average atrial evoked response duration and/or an atrial evoked response duration dispersion, for the period of time.

Steps 302 and 304 are repeated from time to time. In other words, steps 302 and 304 are performed for each of a plurality of periods of time. For examples, steps 302 and 304 can be performed for 60 seconds or 60 cardiac cycles, and repeated every 10 minutes, hour, day, or the like. This is just an example, which is not meant to be limiting. In specific embodiments, steps 302 and 304 are performed when (whenever, or at least some of the times) that atrial automatic capture threshold detection is performed. In other words, in accordance with specific embodiments of the present invention, the plurality of periods of time at which steps 302 and 304 are performed are different times that atrial automatic capture threshold detection is performed. This is not to say that steps 302 and 304 must be performed every time automatic capture threshold detection is performed. Rather, it is possible that automatic capture threshold detection is performed multiple times a day, yet steps 302 and 304 are only performed once a day, for example. It is also possible that steps 302 and 304 are performed at times when atrial pacing is being performed, other than when automatic atrial capture threshold detection is performed. However, this is not to say that steps 302 and 304 must be performed every time the atrium is being paced. Rather, it is possible that the atrium is paced substantially continually, or at least multiple times a day, yet steps 302 and 304 are only performed once a day, for example.

At step 306, a change in the at least one atrial evoked response metric over time is detected based on the information stored at various instances of step 304. Such a change can be an increase, a decrease, or there can be relatively no change. A magnitude of the change can also be determined. For example, at step 306 an average atrial evoked response duration for a second period of time can be compared to an average atrial evoked response duration for a first period of time. Additionally, or alternatively, an average atrial evoked response duration dispersion for the second period of time can be compared to the atrial evoked response duration dispersion for the first period of time. Where multiple atrial evoked response metrics are to be compared at step 306, weighting factors can be used to combine the atrial evoked response metrics or combine the results of multiple comparisons.

At step 308, a change in atrial stretch is monitored based on the detected change in the at least one atrial evoked response over time. Step 308 can include determining whether a patient's atrial stretch has increased, decreased, or stayed relatively the same. This can include interpreting an increase in certain atrial evoked response metrics, such as atrial evoked response duration and/or atrial evoked response duration dispersion, as being indicative of increased atrial stretch, and interpreting decreases in the same atrial evoked response metrics as being indicative of decreases in atrial stretch. Relatively no change in an atrial evoked response metric can be interpreted in relatively no change in atrial stretch. Alternative atrial evoked response metrics may be used. How to interpret increases or decreases in alternative atrial evoked response metrics depends on the metric, and can be determined through experimentation, e.g., from empirical data.

Increases in atrial stretch can be indicative of a worsening in a patient HF condition, and thus, step 308 can also include assessing a patient's HF condition and/or predicting a risk of an acute HF exacerbation, based on the determined change in the at least one atrial evoked response metric. This can include interpreting an increase in atrial stretch (and thus an in certain atrial evoked response metrics, such as atrial evoked response duration and/or atrial evoked response duration dispersion), as being indicative of a worsening HF condition and/or an increased risk of an acute HF exacerbation, and interpreting decreases in atrial stretch (and thus in the same atrial evoked response metrics) as being indicative of an improved HF condition and/or a reduced risk of an acute HF exacerbation. Relatively no change in atrial stretch (and thus in an atrial evoked response metric) can be interpreted in relatively no change in the HF condition and/or the risk of an acute HF exacerbation.

At step 310, a response can be triggered if an increase in atrial stretch exceeds a specified threshold. Alternatively, or additionally, at step 310 a response can be triggered if a change in the at least one atrial evoked response metric is in a direction indicative of an increase in atrial stretch beyond a specified threshold.

If it is determined at step 308 that atrial stretch has increased beyond a specified threshold (and thus, e.g., that a patient has a heightened risk of an acute HF exacerbation, and/or that the patient's HF condition has worsened beyond a specified threshold), then at step 310 an appropriate therapy can be triggered. One type of therapy would be for an implanted device, if appropriately equipped, to deliver appropriate drug therapy. In another embodiment, the implantable device can perform appropriate pacing therapy to attempt to prevent and/or treat an acute heart failure exacerbation. One of ordinary skill in the art would understand from the above description that other responses are also possible, while still being within the spirit and scope of the present invention.

Additionally or alternatively, a patient can be alerted (e.g., using alert 219) at step 310 if it was determined at step 308 that an increase in atrial stretch exceeded a specific threshold (and thus, e.g., that there is a detection of a heightened risk of an acute HF exacerbation). An alert could be a vibratory or auditory alert that originates from within the implantable device 110. Alternatively, the implantable device 110 may wirelessly transmit an alert to an external device (e.g., 202) that produces a visual or auditory alert that a patient can see or hear. The alert may inform that patient that he should rest, or if the patient is operating some type of dangerous machinery (e.g., a car), that the patient should stop what they are doing. By alerting the patient to rest, it is possible an HF exacerbation may be avoided, or if it does occur, the patient will be less dangerous to themselves and others if the patient is resting when the exacerbation occurs (as opposed, e.g., to driving a car). It is also possible that the alert can be generated by an external device (e.g., 202).

Additionally or alternatively, the patient can be instructed to take medication when alerted. Additionally or alternatively, a caregiver (e.g., physician) can be alerted if it is determined that the patient has atrial stretch, or an increase therein, beyond a threshold (and thus, e.g., is at a heightened risk of an acute HF exacerbation). Additionally or alternatively, information related to atrial evoked response metric(s) and/or changes therein can be stored. This can include, for example, storing amplitude, slope, timing, and/or duration information relating to the atrial evoked response metrics and/or dispersion information for any of the aforementioned metrics. If such information is stored in an implanted device, such information can be continually, or from time to time, automatically uploaded to an external device (e.g., 202). Such an external device 202 can be located, e.g., in the patient's home, and the information can be transmitted (e.g., through telephone lines or the Internet) to a medical facility where a physician can analyze the information. For example, the external device 202 can be a bedside monitor, or an ambulatory device that the patient carries with them. Alternatively, the external device 202 can be an external programmer located at a medical facility, and the information can be uploaded when the patient visits the facility.

As described above in the Background, chronic diseases such as CHF require close medical management to reduce morbidity and mortality. However, the conventional approach of periodic patient follow-ups has proved unsatisfactory, as life-threatening exacerbations can develop between physician follow-up examinations. Further, if a developing HF exacerbation is recognized early, it can be more easily and inexpensively terminated, typically with a modest increase in oral diuretic. However, if it develops beyond the initial phase, an acute heart failure exacerbation becomes difficult to control and terminate. Hospitalization in an intensive care unit is often required. It is during an acute exacerbation of heart failure that many patients succumb to the disease.

Further, it is often difficult for patients to recognize a developing HF exacerbation, despite the presence of numerous physical signs that would allow a physician to readily detect it. Furthermore, since exacerbations typically develop over hours to days, even frequently scheduled routine follow-up with a physician cannot effectively detect most developing exacerbations. It is therefore desirable to have a system that allows for routine, frequent monitoring of patients so that an exacerbation can be recognized early in its course. With the patient and/or physician thus notified by the monitoring system of the need for medical intervention, a developing exacerbation can more easily and inexpensively be terminated early in its course.

LAP, PCWP and RPAP

As mentioned above in the Background, there is a desire to provide relatively accurate and efficient systems and methods for monitoring LAP, PCWP and/or RPAP. As described in the background, typical techniques for measuring LAP, PCWP and RPAP are invasive, time consuming, and do not lend themselves to chronic use.

Figure 4:
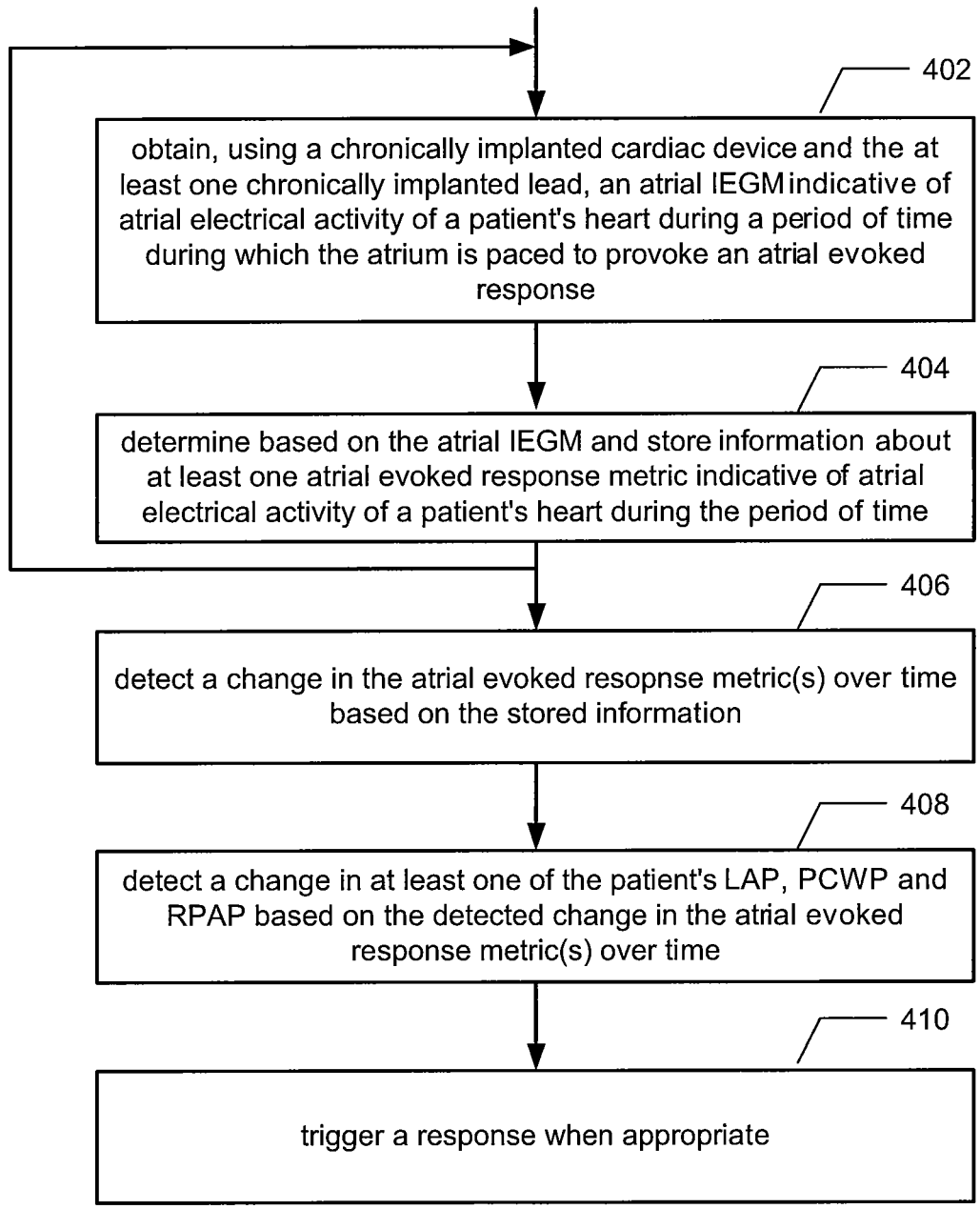
FIG. 4 is a high level flow diagram that is used to summarize specific embodiments of the present invention that can be used to detect changes in a patient's LAP, PCWP and/or RPAP.

The high level flow diagram of FIG. 4 will now be used to describe methods for use by an implanted system including a chronically implanted cardiac device and at least one chronically implanted lead, for monitoring changes a patient's LAP, PCWP and/or RPAP. Embodiments of the present invention are also directed to chronically implanted systems that can implement such methods.

Referring to FIG. 4, at step 402, a chronically implanted cardiac device and at least one chronically implanted lead are used to obtain an atrial IEGM indicative of electrical activity of a patient's heart during a period of time. At step 404, based on the atrial IEGM there is a determination of atrial evoked response metric(s) indicative of atrial electrical activity during the period of time, and information about such atrial evoked response metric(s) is stored, e.g., in memory 294 of FIG. 2. At step 406, a change in the at least one atrial evoked response metric over time is detected based on the information stored at various instances of step 404. Such a change can be an increase, a decrease, or there can be relatively no change. Since steps 402-406 are substantially similar to steps 302-306, additional details of steps 402-406 can be appreciated from the description of steps 302-306 provided above with reference to FIG. 3.

At step 408, a change in the patient's LAP, PCWP and/or RPAP is detected based on the detected change in the at least one atrial evoked response metric over time. Step 408 can include determining whether a patient's LAP, PCWP and/or RPAP has increased, decreased, or stayed relatively the same. This can include interpreting an increase in certain atrial evoked response metrics, such as atrial evoked response duration and/or atrial evoked response duration dispersion, as being indicative of an increase in LAP and PCWP and/or RPAP, and interpreting decreases in the same atrial evoked response metrics as being indicative of a decrease in LAP, PCWP and/or RPAP. Relatively no change in a atrial evoked response metric can be interpreted in relatively no change in the LAP, PCWP and/or RPAP. Where alternative atrial evoked response metrics are monitored, it may be that an increase in the metric is indicative of a decrease in LAP, PCWP and/or RPAP, and vice versa. Alternative atrial evoked response metrics may be used. How to interpret increases or decreases in alternative atrial evoked response metrics depends on the metric, and can be determined through experimentation, e.g., from empirical data.

At step 410, a response can be triggered if a change in the patient's LAP, PCWP and/or RPAP exceeds a specified threshold. One type of therapy would be for an implanted device, if appropriately equipped, to deliver appropriate drug therapy. For example, the device can titrate a dose of diuretic drugs and other drugs. Additionally or alternatively, a patient can be alerted (e.g., using alert 219) at step 410. Alternatively, the implantable device 110 may wirelessly transmit an alert to an external device (e.g., 202) that produces a visual or auditory alert that a patient can see or hear. Additionally or alternatively, the patient can be instructed to take medication when alerted.

Additionally or alternatively, at step 410 a caregiver (e.g., physician) can be alerted if it is determined that the patient's LAP, PCWP and/or RPAP is too high or too low. Additionally or alternatively, information related to atrial evoked response metric(s) and/or changes therein can be stored. This can include, for example, storing amplitude, slope, area, timing, and/or duration information relating to the atrial evoked response and/or dispersion information for any of the aforementioned metrics. If such information is stored in an implanted device, such information can be continually, or from time to time, automatically uploaded to an external device (e.g., 202). Such an external device 202 can be located, e.g., in the patient's home, and the information can be transmitted (e.g., through telephone lines or the Internet) to a medical facility where a physician can analyze the information. For example, the external device 202 can be a bedside monitor, or an ambulatory device that the patient carries with them. Alternatively, the external device 202 can be an external programmer located at a medical facility, and the information can be uploaded when the patient visits the facility.

AF

As mentioned above in the Background, AF is often asymptomatic and intermittent, which typically results in appropriate diagnosis and/or treatment not occurring in a timely manner. To overcome this, it is desired that a cardiac device monitors for AF. Further, it is also desirable to predict a risk of AF, so that preventative measures can be delivered.

Figure 5:
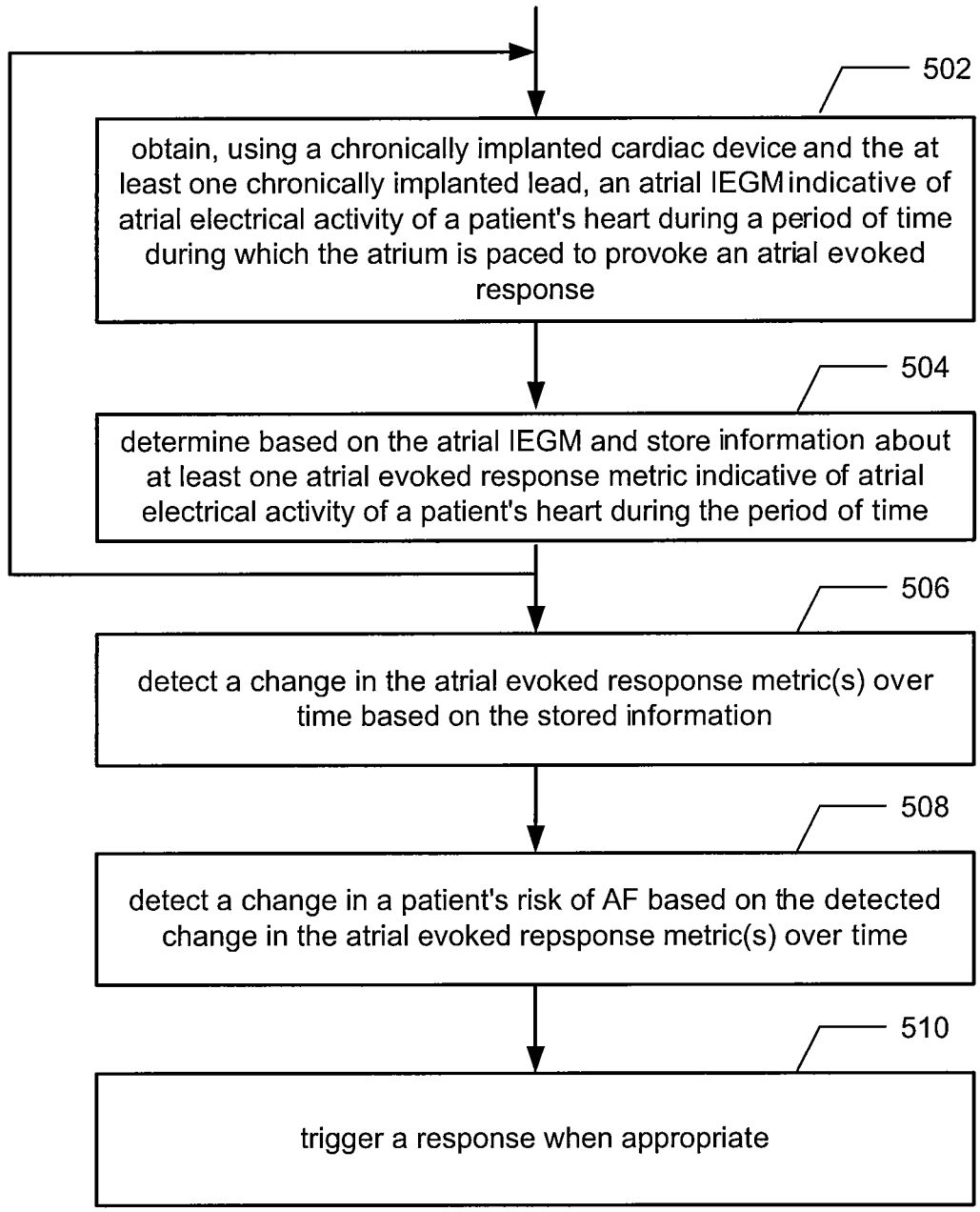
FIG. 5 is a high level flow diagram that is used to summarize specific embodiments of the present invention that can be used to detect changes in a patient's risk of AF.

The high level flow diagram of FIG. 5 will now be used to describe methods for use by an implanted system including a chronically implanted cardiac device and at least one chronically implanted lead, for monitoring changes a patient's risk of AF. Embodiments of the present invention are also directed to chronically implanted systems that can implement such methods.

Referring to FIG. 5, at step 502, a chronically implanted cardiac device and the at least one chronically implanted lead are used to obtain an atrial IEGM indicative of electrical activity of a patient's heart during a period of time. At step 504, based on the atrial IEGM there is a determination of atrial evoked response metric(s) indicative of atrial electrical activity during the period of time, and information about such atrial evoked response metric(s) is stored, e.g., in memory 294 of FIG. 2. At step 506, a change in the at least one atrial evoked response metric over time is detected based on the information stored at various instances of step 504. Such a change can be an increase, a decrease, or there can be relatively no change. Since steps 502-506 are substantially similar to steps 302-306, additional details of steps 502-506 can be appreciated from the description of steps 302-306 provided above with reference to FIG. 3.

At step 508, a change in the patient's risk of AF is detected based on the detected change in the at least one atrial evoked response metric over time. Step 508 can include determining whether a patient's risk of AF has increased, decreased, or stayed relatively the same. This can include interpreting an increase in certain atrial evoked response metrics, such as atrial evoked response duration and/or atrial evoked response duration dispersion, as being indicative of an increased risk of AF, and interpreting decreases in the same atrial evoked response metrics as being indicative of a decreased risk of AF. Relatively no change in a atrial evoked response metric can be interpreted as relatively no change in the risk of AF. Where alternative atrial evoked response metrics are monitored, it may be that an increase in the metric is indicative of a decrease in risk of AF, and vice versa. How to interpret increases or decreases in alternative atrial evoked response metrics (including dispersions of such metrics) depends on the metric, and can be determined through experimentation, e.g., from empirical data.

At step 510, a response can be triggered if a change in the patient's risk of AF exceeds a specified threshold. One type of therapy would be for an implanted device, if appropriately equipped, to deliver appropriate drug therapy. Additionally or alternatively, a patient can be alerted (e.g., using alert 219) at step 510. Alternatively, the implantable device 110 may wirelessly transmit an alert to an external device (e.g., 202) that produces a visual or auditory alert that a patient can see or hear. The alert may inform that patient that he should rest, or if the patient is operating some type of dangerous machinery (e.g., a car), that the patient should stop what they are doing. By alerting the patient to rest, it is possible that AF may be avoided, or if it does occur, the patient will be less dangerous to themselves and others if the patient is resting when the arrhythmia occurs (as opposed, e.g., to driving a car). It is also possible that the alert can be generated by an external device (e.g., 202).

Additionally, or alternatively, atrial anti-tachycardia pacing (AATP) can be delivered at step 510 to prevent AF. Additionally, or alternatively, one or more atrial vagal fat pad can be stimulated. In a specific embodiment, atrial vagal fat pad stimulation can be delivered to inhibit atrial vagal fat pad activation, to thereby prevent AF, as described in more detail in U.S. patent Ser. No. 11/615,448 (Ryu et al.), filed Dec. 22, 2006, entitled "Neurostimulation and Neurosensing Techniques to Optimize Atrial Anti-Tachycardia Pacing For Prevention of Atrial Tachyarrhythmias", which is incorporated herein by reference. Alternatively, subexcitatory stimulation and/or excitatory stimulation can be delivered to one or more atrial vagal fat pad to thereby prevent AF, as described in U.S. patent Ser. No. 11/615,497 (Ryu et al.) entitled "Neurostimulation and Neurosensing Techniques to Optimize Atrial Anti-Tachycardia Pacing for Prevention of Atrial Tachyarrhythmias," which is incorporated herein by reference. Other responses are also possible, and within the scope of embodiments of the present invention.

Atrial Pacing Energy Level

Specific embodiments of the present invention relate to selecting a preferred atrial pacing energy level. As briefly discussed above, a goal of atrial automatic capture threshold detection is to adjust the stimulation energy delivered to the atrium so that it is at a level that will reliably capture the atrium without wasting energy. This is typically accomplished by determining, from time to time, the atrial capture threshold level and pacing the atrium at a level equal to the atrial capture threshold level, or more likely, equal to the atrial capture threshold level plus a specified margin, e.g., a safety margin or working margin. A safety margin can be defined, e.g., as a ratio (e.g., 2:1 or 3:1) or percentage (e.g., 150% or 200%) relative to the measured atrial capture threshold. A working margin can be defined, e.g., as a fixed amount (e.g., 0.25V) added to the measured atrial capture threshold. Typically, a device will pace the atrium at the capture threshold plus the specified margin, not taking into account other factors. In contrast, in accordance with the embodiments of the present invention described with reference to FIG. 6, atrial pacing may occur at a somewhat higher level if the result is a reduction in atrial stretch, an improved HF condition and/or a reduced risk of AF.

Figure 6:
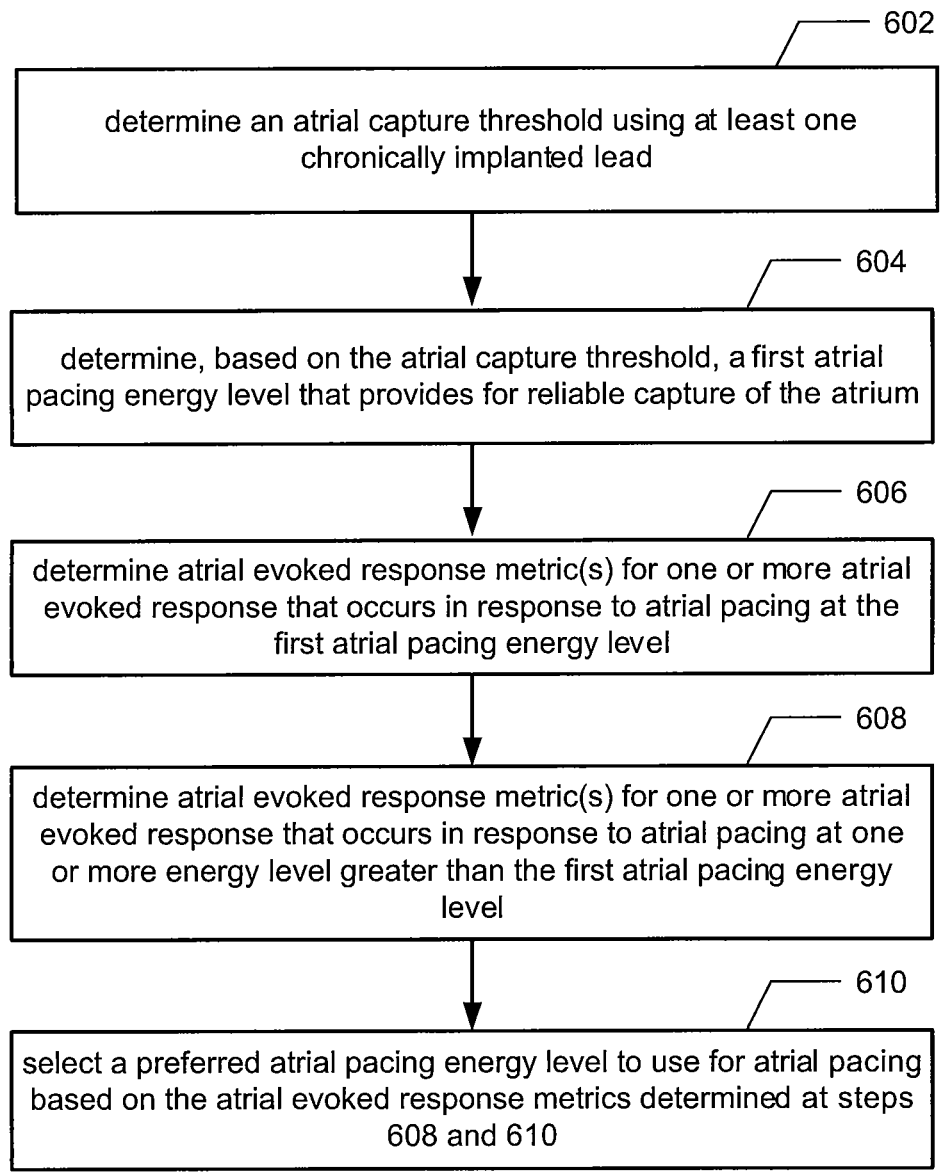
FIG. 6 is a high level flow diagram that is used to summarize specific embodiments of the present invention that can be used to select a pacing energy level taking into account whether an increased energy level results is a reduction in atrial stretch, an improved HF condition and/or reduced risk of AF.

Referring to FIG. 6, at a step 602, an atrial capture threshold for pacing in the atrium is determined using at least one chronically implanted lead. As explained above, the atrial capture threshold represents the amount of electrical energy required cause atrial depolarization. There are various well known ways to determine the atrial capture threshold, and thus, this step need not be described in additional detail.

At step 604, a first atrial pacing energy level that provides for reliable capture of the atrium is determined based on the atrial capture threshold determined at step 602. As was discussed above, this energy level can be the atrial capture threshold level, or the atrial capture threshold level plus a specified margin, e.g., a safety or working margin.

At step 606, at least one atrial evoked response metric is determined for one or more atrial evoked response (also known as a paced atrial event) that occurs in response to atrial pacing at a first energy level specified based on the determined atrial capture threshold. As was discussed above with reference to FIG. 3, exemplary atrial evoked response metrics that can be measured include atrial evoked response maximum amplitude (atrial evoked response max), atrial evoked response minimum amplitude (atrial evoked response min), atrial evoked response peak-to-peak amplitude, atrial evoked response duration, atrial evoked response area, atrial evoked response slope, and atrial evoked response timing, and/or the dispersion of any of the aforementioned metric. Preferably such atrial evoked response metric(s) is/are determined for a plurality of paced atrial events that occurs in response to atrial pacing at the first atrial pacing energy level, and the metrics are combined, e.g., averaged, summed, or the like, to reduce the affects of noise and motion artifacts on such measurements.

At step 608, at least one atrial evoked response metric is determined for one or more atrial evoked response (also known as a paced atrial event) that occurs in response to atrial pacing at one or more energy level greater than the first atrial pacing energy level. For example, the one or more energy level (greater than the first atrial pacing energy level) can be one or more percentage of the first atrial pacing energy level (e.g., 110%, 120% and 130% of the first atrial pacing energy level), or one or more fixed voltage level above the first atrial pacing energy level (e.g., 0.25V, 0.50V and 0.75V). These are just a few examples, which are not meant to be limiting.

The determining of the at least one atrial evoked response metric at step 606 can occur during the determining of the atrial capture threshold at step 602, e.g., if energy levels above the actual capture threshold are tested during the search for the atrial capture threshold. Similarly, the determining of the at least one atrial evoked response metric at step 608 can occur during the determining of the atrial capture threshold at step 602, e.g., if energy levels above the actual capture threshold and above the first atrial pacing energy level are also tested during the search for the atrial capture threshold.

At step 610, a preferred atrial pacing energy level to use for atrial pacing is determined (e.g., selected) based on the atrial evoked response metrics determined at steps 606 and 608. At step 610 an atrial pacing energy level greater than the first atrial pacing energy level (determined at step 604) can be selected as the preferred atrial pacing energy level, if it is determined based on atrial evoked response metrics (determined at step 606 and 608) that pacing at an energy level greater than the first atrial pacing energy level would reduce atrial stretch, improve the patient's HF condition and/or reduce the patient's risk of AF. Exemplary techniques for determining the patient's atrial stretch, HF condition and/or risk of AF based on atrial evoked response metric(s) were discussed above with reference to FIGS. 3 and 5, respectively.

In the embodiment of FIG. 6, a pacing energy level that is higher than is necessary for reliable capture may be selected if the higher energy level provides for a reduction in atrial stretch, an improved HF condition and/or a lower risk of AF. The extent of the reduction in atrial stretch, the improvement in HF condition and/or the extent of the reduction in risk of AF can be used to determine whether it's worth increasing the pacing energy level, because the higher the pacing energy level the shorter the battery life. Various algorithms can be developed that enable a cardiac device to make such decisions, e.g., based on programmed preferences of a physician. Alternatively, a physician can make such a determination.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. without substantially changing the overall events and results.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A method for monitoring atrial stretch, for use by an implanted system including a chronically implanted cardiac device and at least one chronically implanted lead, the method comprising:
   (a) for each of a plurality of periods of time during which the atrium is paced to provoke an atrial evoked response
      (a.1) obtaining, using the chronically implanted cardiac device and the at least one chronically implanted lead, an atrial intracardiac electrogram (IEGM) indicative of atrial electrical activity of a patient's heart during the period of time; and
      (a.2) determining based on the atrial IEGM and storing information about at least one atrial evoked response metric indicative of atrial electrical activity during the period of time;
   (b) detecting, based on the stored information, a change in the at least one atrial evoked response metric over time; and
   (c) monitoring atrial stretch based on the detected change in the at least one atrial evoked response metric over time.

2. The method of claim 1, wherein the plurality of periods of time during which the atrium is paced to provoke an atrial evoked response are different times that atrial automatic capture threshold detection is performed.

3. The method of claim 1, further comprising:
   (d) detecting a change in a patient's heart failure (HF) condition based on the monitored atrial stretch.

4. The method of claim 1, further comprising:
   (d) triggering a response if a change in the at least one atrial evoked response metric is in a direction indicative of an increase in atrial stretch beyond a specified threshold.

5. The method of claim 1, wherein step (c) includes predicting a risk of an acute HF exacerbation based on the monitored atrial stretch.

6. The method of claim 1, wherein the at least one atrial evoked response metric includes at least one of the following:

atrial evoked response duration; and
atrial evoked response duration dispersion.

7. The method of claim 1, wherein the at least one atrial evoked response metric is selected from the group consisting of:
   atrial evoked response maximum amplitude;
   atrial evoked response minimum amplitude;
   atrial evoked response peak-to-peak amplitude;
   atrial evoked response area;
   atrial evoked response slope;
   atrial evoked response timing;
   atrial evoked response maximum amplitude dispersion;
   atrial evoked response minimum amplitude dispersion;
   atrial evoked response peak-to-peak amplitude dispersion;
   atrial evoked response area dispersion;
   atrial evoked response slope dispersion; and
   atrial evoked response timing dispersion.

8. The method of claim 1, further comprising:
   detecting a change in the patient's risk of atrial fibrillation (AF) based on the monitored atrial stretch.

9. An implantable system for monitoring a patient's atrial stretch, comprising:
   a sensing circuit, connectable to electrodes of at least one chronically implanted lead, and configured to obtain an atrial intracardiac electrogram (IEGM) indicative of atrial electrical activity of a patient's heart for each of a plurality of periods of time during which the atrium is paced to provoke an atrial evoked response;
   an atrial evoked response monitor configured to determine, based on the atrial IEGM, at least one atrial evoked response metric indicative of atrial electrical activity for each of the plurality of periods of time;
   memory to store information about the about at least one atrial evoked response metric determined for each of the plurality of periods of time; and
   an atrial stretch monitor configured to
      detect, based on the stored information, a change in the at least one atrial evoked response metric over time; and
      detect a change in the patient's atrial stretch based on the detected change in the at least one atrial evoked response metric over time.

10. The implantable system of claim 9, wherein the plurality of periods of time during which the atrium is paced to provoke an atrial evoked response are different times that atrial automatic capture threshold detection is performed by the implantable system.

11. A method for estimating a change in at least one of a patient's left atrial pressure (LAP), the patient's pulmonary capillary wedge pressure (PCWP), and the patient's right pulmonary artery pressure (RPAP) for use by an implanted system including a chronically implanted cardiac device and at least one chronically implanted lead, the method comprising:
   (a) for each of a plurality of periods of time during which the atrium is paced to provoke an atrial evoked response
      (a.1) obtaining, using the chronically implanted cardiac device and the at least one chronically implanted lead, an arterial intracardiac electrogram (IEGM) indicative of atrial electrical activity of a patient's heart during the period of time; and
      (a.2) determining based on the atrial IEGM and storing information about at least one atrial evoked response metric indicative of atrial electrical activity during the period of time;

(b) detecting, based on the stored information, a change in the at least one atrial evoked response metric over time; and (c) detecting a change in at least one of the patient's LAP, PCWP and RPAP based on the detected change in the at least one atrial evoked response metric over time.

12. The method of claim 11, wherein the plurality of periods of time during which the atrium is paced to provoke an atrial evoked response are different times that atrial automatic capture threshold detection is performed.

13. The method of claim 11, wherein the at least one atrial evoked response metric includes at least one of the following:
   atrial evoked response duration; and
   atrial evoked response duration dispersion.

14. The method of claim 11, wherein the at least one atrial evoked response metric includes at least one of the following:
   atrial evoked response maximum amplitude;
   atrial evoked response minimum amplitude;
   atrial evoked response peak-to-peak amplitude;
   atrial evoked response area;
   atrial evoked response slope;
   atrial evoked response timing;
   atrial evoked response maximum amplitude dispersion;
   atrial evoked response minimum amplitude dispersion;
   atrial evoked response peak-to-peak amplitude dispersion;
   atrial evoked response area dispersion;
   atrial evoked response slope dispersion; and
   atrial evoked response timing dispersion.

15. A method monitoring a patient's risk of atrial fibrillation (AF), for use by an implanted system including a chronically implanted cardiac device and at least one chronically implanted lead, the method comprising:
   (a) for each of a plurality of periods of time during which the atrium is paced to provoke an atrial evoked response
      (a.1) obtaining, using the chronically implanted cardiac device and the at least one chronically implanted lead, an intracardiac electrogram (IEGM) indicative of atrial electrical activity of a patient's heart during the period of time; and
      (a.2) determining based on the atrial IEGM and storing information about at least one atrial evoked response metric indicative of atrial electrical activity during the period of time;
   (b) detecting, based on the stored information, a change in the at least one atrial evoked response metric over time; and
   (c) detecting a change in a patient's risk of AF based on the detected change in the at least one atrial evoked response metric over time.

16. The method of claim 15, wherein the plurality of periods of time during which the atrium is paced to provoke an atrial evoked response are different times that atrial automatic capture threshold detection is performed.

17. The method of claim 15, further comprising:
   (d) triggering a response if the change in the patient's risk of AF exceeds a specified threshold.

18. The method of claim 15, further comprising:
   (d) triggering a response if the determined change in the at least one atrial evoked response metric is in a direction indicative of an increased risk of AF and beyond a specified threshold.

19. A method for selecting a preferred atrial pacing energy level, for use by an implanted system including a chronically implanted cardiac device and at least one chronically implanted lead, the method comprising:
   (a) determining an atrial capture threshold for pacing in the atrium using the at least one chronically implanted lead;
   (b) determining, based on the atrial capture threshold, a first atrial pacing energy level that provides for reliable capture of the atrium;
   (c) determining at least one atrial evoked response metric for one or more atrial evoked response that occurs in response to atrial pacing at the first atrial pacing energy level;
   (d) determining at least one atrial evoked response for one or more atrial evoked response that occurs in response to atrial pacing at one or more energy level greater than the first atrial pacing energy level; and
   (e) selecting a preferred atrial pacing energy level to use for atrial pacing based on the atrial evoked response metrics determined at (c) and (d), wherein step (e) includes selecting an atrial pacing energy level greater than the first atrial pacing energy level as the preferred atrial pacing energy level, if using the energy level greater than the first atrial pacing energy level provides at least one of the following:
   a reduction in atrial stretch,
   an improved heart failure (HF) condition, and
   a reduction in the patient's risk of atrial fibrillation (AF).

20. The method of claim 19, wherein step (b) comprises determining the first atrial pacing energy level by adding a safety margin, a working margin or some other margin to the atrial capture threshold determined at step (a).

21. The method of claim 19, wherein a measurement for determining the at least one atrial evoked response metric at step (c) can occur during the determining of the atrial capture threshold at step (a).

22. The method of claim 19, wherein a measurement for determining the at least one atrial evoked response metric at step (d) can occur during the determining of the atrial capture threshold at step (a).

* * * * *